Figure 1:
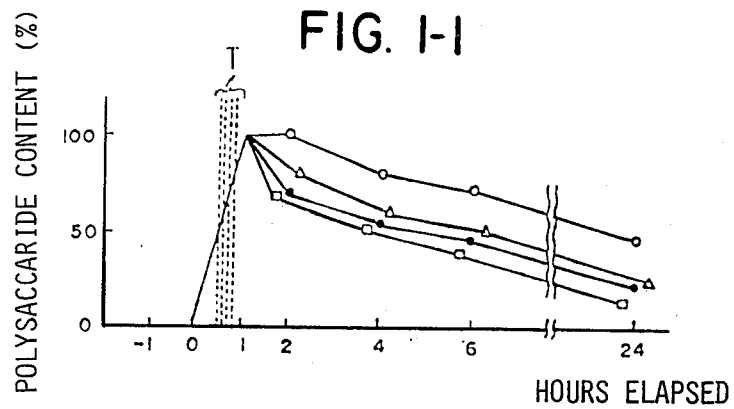

United States Patent [19]

Igarashi et al.

[11] 4,370,472

[45] Jan. 25, 1983

[54] PLASMA EXPANDER

[75] Inventors: Toshiji Igarashi, Tokorozawa; Keiichi Nomura, Hohya; Kunji Naito; Mikihiko Yoshida, both of Okayama, all of Japan

[73] Assignee: Hayashibara Biochemical Laboratories, Inc., Okayama, Japan

[21] Appl. No.: 152,151

[22] Filed: May 21, 1980

[30] Foreign Application Priority Data

May 25, 1979 [JP] Japan .................................. 54-63976

[51] Int. Cl.³ ...................... A61K 31/715; C07H 1/08
[52] U.S. Cl. ..................................... 536/1.1; 424/180
[58] Field of Search ............................. 536/1; 424/180

[56] References Cited

U.S. PATENT DOCUMENTS 3,912,591 10/1975 Kato et al. ............................ 195/31

FOREIGN PATENT DOCUMENTS 51-42199 11/1976 Japan .

*Primary Examiner*—John M. Ford
*Attorney, Agent, or Firm*—Wenderoth, Lind & Ponack

[57] ABSTRACT

Novel plasma expander which consists of a refined pullulan having a narrow molecular weight distribution falling within the range of from 30,000 to 90,000; preparation of said plasma expander in a form suitable for intravenous injection in surgical operation and prevention of hemorrhage; and isolation of said refined pullulan from the conventional pullulan which possesses the molecular weight distribution broader than that mentioned above.

3 Claims, 11 Drawing Figures

- PUL-50
- PUL-85
- DEX-40
- H E S-200

T    TIME (20 MIN.) FOR 75 ML INFUSION

- PUL-50
- PUL-85
- DEX-40
- H E S-200

T TIMES (MIN.) FOR 75 ML INFUSION

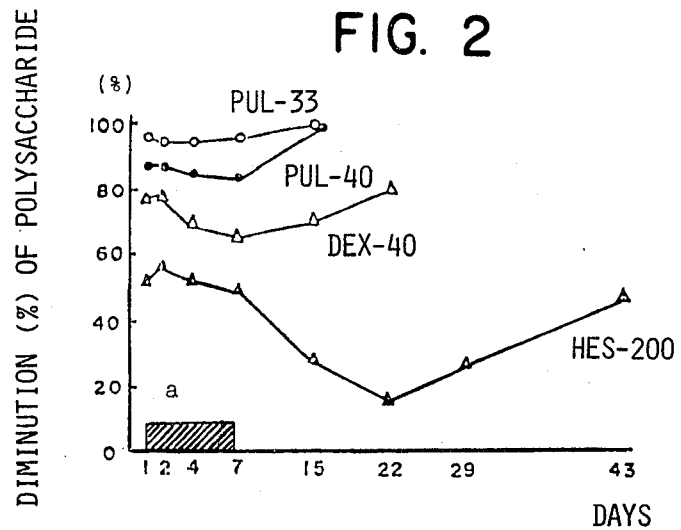
A ... 40 ML/KG/DAY FOR SEVEN INFUSIONS
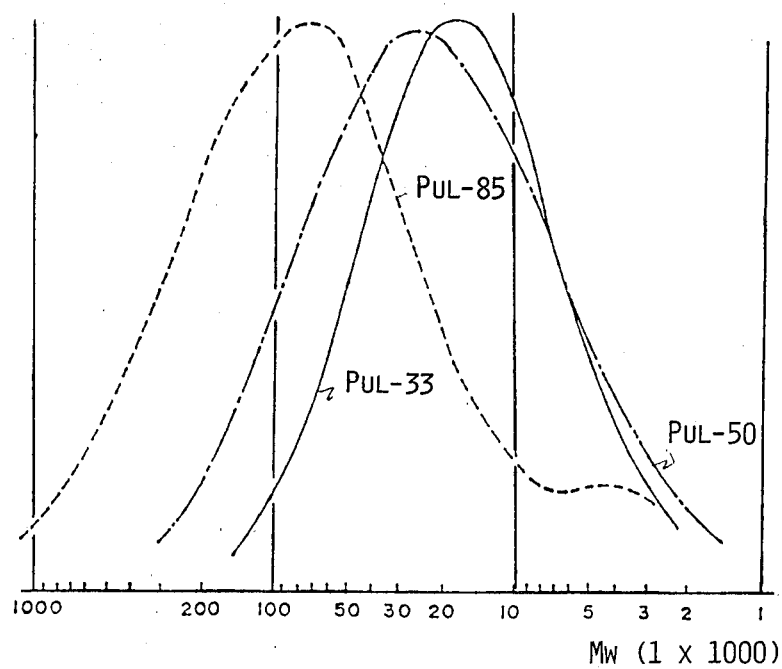

A POLYSACCHARIDE DERIVED FROM PUL-33
B POLYSACCHARIDE DERIVED FROM PUL-50
C POLYSACCHARIDE DERIVED FROM PUL-85

X CULTIVATION IN PLAIN SALINE (CONTROL)
O CULTIVATION WITH KIDNEY HOMOGENATE
● CULTIVATION WITH LUNG HOMOGENATE
P PROPORTIONS OF ETHANOL : WATER

X CULTIVATION IN PLAIN SALINE (CONTROL)
O CULTIVATION WITH KIDNEY HOMOGENATE
● CULTIVATION WITH LUNG HOMOGENATE
P PROPORTIONS OF ETHANOL : WATER

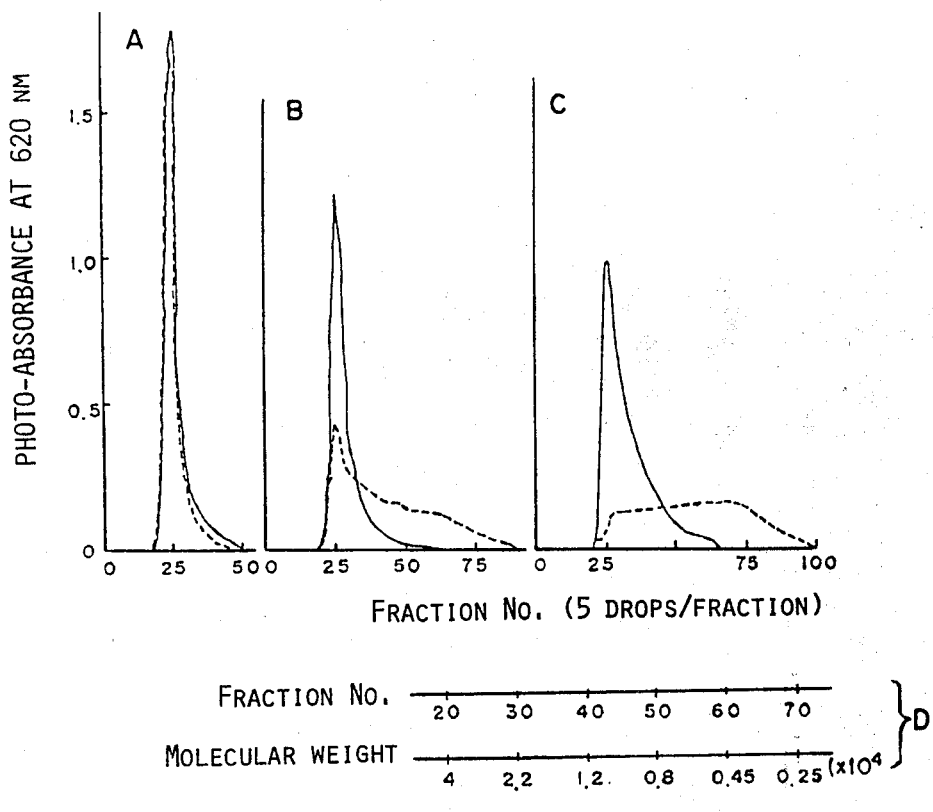

A ... CULTIVATION IN PLAIN SALINE (CONTROL)
B ... CULTIVATION WITH KIDNEY HOMOGENATE
C ... CULTIVATION WITH LUNG HOMOGENATE

PLASMA EXPANDER

This invention relates to a plasma expander, the colloidal component of which consists of a refined pullulan having a specifically confined molecular weight distribution falling within the range of from 30,000 to 90,000.

The plasma expander of the present invention is useful for prevention and treatment of hemorrhage.

The plasma expander of the invention can be repeatedly administered through intravenous injection to a patient with excellent safety, because the pullulan contained therein, when infused, can be metabolized and decomposed in the body to such an extent that it is excreted completely through the kidneys.

Recently, utility of plasma expanders for the treatment of an external wound and for surgical operations has been increased, inasmuch as there is a risk of probable serum hepatitis caused by blood transfusion and a limited supply of blood for transfusion.

The commercially available plasma expanders, used at present consist of colloidal components such as modified gelatin, dextran and hydroxyethyl starch hereinunder called "H E S".

The requirements for colloidal substances adapted for use as a plasma expander are:

(a) They should have molecular dimensions which guarantee an adequate collodial osmotic effect.

(b) The aqueous solution thereof should have a colloidal osmotic pressure and a viscosity of the same order of magnitudes as those of the plasma.

(c) They should be as compatible with to the body as possible and have no toxic properties. They should cause no injury by being stored up in the tissues and organs of the body, but should be eliminated from the body through metabolism and/or decomposition.

(d) They should remain in the blood for a sufficiently long period of time and at a concentration adequate to warrant a desired therapeutic effect.

(e) The aqueous solution thereof should not develop pyrogenic or allergic reactions. It should not develop sensitivity through antigenic properties.

(f) They should have no tendency to cause agglutination of lysis of erythrocytes or damage to leucocytes. They should not interfere seriously with blood grouping.

(g) They should be metabolized and ultimately eliminated from the body in such a way as to cause no delayed interference with the function of any of the organs, even after repeated administrations.

The known plasma expanders which are commercially available do not meet the abovementioned requisites because they not only do not show an expected plasma expanding effect, but also are toxic owing to their accumulation in the body for an prolonged time without metabolism.

More particularly, the deficiencies pointed out on the hitherto known plasma expander are:

(a) Physical and chemical properties of the modified gelatin are not sufficiently made evident, and since the greater portion of its content in the therapeutic preparation are excreted through the kidney within two or three hours, the expected plasma expanding effect does not last long enough.

(b) Risk of causing thrombosis had been reported in the use of the commerically available dextran preparations as plasma expander such as Dex-70, for example, which contains the dextran having the average molecular weight ($\overline{Mw}$) of around 70,000, because said preparation has a tendency of causing agglutination of red cells and blood in the vessels.

(c) Dex-40, another dextran preparation, which contains dextran having $\overline{Mw}$ of around 40,000, and has been used most frequently at present, is, owing to its small size of the molecule, liable to be quickly filtered through the renal glomerulus, inducing an osmotic diuresis. As the result, there is a tendency of occurrence of osmotic nephritis when the same is used repeatedly.

(d) It is said that H E S includes the molecular constituents having various molecular sizes. Among them, the constituents of the smaller molecular sizes are easily excretable through the kidney when infused, while the constituents of the extremely large molecular sizes are liable to remain as they are in the body, and accordingly, there is a risk of inducing renal damage.

Under the circumstances, the inventors of the present invention attempted to find a novel plasma expander which possesses the desired therapeutic effect without undesired side-effects. As the result of thorough investigations especially on pullulan, the inventors surprisingly found that pullulan having an falling within the range of from 30,000 to 90,000 is highly effective, with safety, as a plasma expander.

Namely, the pullulan having the said particular molecular weight, when infused in the body in a form of an aqueous preparation in a concentration of 4–10% (w/v), shows a notable plasma expanding effect with almost no accumulation in the body. In this connection, it should be added that the pullulan of the above-defined relatively large molecular sizes, which is somewhat difficult to excrete through the renal glomerulus, receives an enzymetic metabolism in the body.

Pullulan is generally produced by cultivation of *Aureobasidium pullulans* in a nutrient medium which contains sugar substance derived from starch through hydrolysis thereof. The pullulan thus obtained is an α-glucan of a broad molecular coverage composed of maltotriose units linked in the α-1,6- and head-to-tail fashions.

The particular pullulan having the formerly defined narrow molecular weight distribution in the present invention can be obtained either by adequately controlling the working conditions in the step of cultivation in the sugar-containing nutrient medium of the abovementioned *Aureobasidium pullulans* in accordance with a conventional method such as that disclosed in Japanese Patent Publication No. 42199/76, (corresponding to U.S. Pat. No. 3,912,591), for example; by partial hydrolysis of a conventional pullulan, which contains a variety of molecular weights inclusive of those higher and lower than those specified in the present invention, using an acid such as hydrochloric, sulfuric, oxalic or the like; by a partition method in which a conventional pullulan is subjected to fractionation using a water-miscible organic solvent such as methanol, ethanol, acetone and isopropanol; or by a chromatographic separation of a conventional pullulan using an adsorbant; or by ultrafiltration.

In this connection, the method of fractionation of a raw pullulan by treating it with the water-miscible organic solvent is particularly recommended over the other methods because of its simplicity.

This method is advantageously carried out by adding one of the above-mentioned water-miscible organic solvents to an about 5-20% aqueous solution of a commercially available pullulan, for example, having a molecular weight distribution broader than that of the refined pullulan specified in the present invention, to produce an aqueous mixture which contains approximately 20-50% (V/V) of said organic solvent; discarding the lower portion of the column of said aqueous mixture to recover the upper portion thereof; adding again to the recovered aqueous mixture the same organic solvent as that used in the preceding step in an amount sufficient to produce the aqueous mixture which contains approximately 40-70% (V/V) of said organic solvent; and recovering finally from the aqueous mixture of the lower portion the objective pullulan defined in the present invention.

By employing any one of the abovementioned several methods for the fractionation of a crude pullulan, the pullulan fractions having the molecular weights falling within the range of the above specifically defined molecular weights are selectively isolated and collected for the purpose of the present invention. This is essential because pullulan having a molecular weight less than 30,000, which corresponds to the lower limit in the above-defined range, when the same is infused intravenously into the body, remains in the blood circulating system only for a limited duration of time resulting in a short lasting plasma expanding effect; whereas pullulan having a molecular weight higher than 90,000, which corresponds to the upper limit in the above-defined molecular weight range, when the same is infused intravenously into the body, has a tendency of giving an undue physical load to the cardiovascular system. None of these defects exist when the pullulan fractions having the said specified molecular weights are selectively used for the infusion.

A pharmaceutical preparation of the present invention to be used for intravenous infusion, which contains approximately 4% to 10% (W/V) of the abovementioned specific pullulan fractions, can be made in accordance with a conventional procedure in the art by dissolving, for example, said pullulan into an isotonic water to produce an aqueous solution which contains the pullulan at the concentration abovementioned, and sterilizing the solution.

Similar pharmaceutical preparations can be obtained either by simultaneously dissolving said specific pullulan in a definite volume of water and an isotonic agent, both in the amounts equivalent to those used in the preparation given in the preceding paragraph; or by dissolving first the pullulan and then the isotonic agent into the definite volume of water, or vice versa, both the substances being used in the amounts equivalent to those in the former case. In the two cases the resulting aqueous solutions are finally sterilized.

As the isotonic agent suitable for the abovementioned purpose, there may be enumerated sodium chloride, Ringer's-type mixed salts to which acetic acid has been added, glucose, sodium chloride mixed with glucose, sorbitol, xylitol and the like.

In mixing the therapeutic preparations such as those abovementioned, it is recommended to previously remove pyrogen from the specific pullulan by treating it with an active carbon.

The following disclosures are concerned with tests for toxicity on the specific pullulan of the present invention.

Several preparations, which had been made in accordance with the aforementioned procedures, and contain the specifically refined pullulan fraction in a physiological saline at a concentration of from 4% to 10% (W/V), were separately infused into auricular veins of rabbits in the quantities of from 30 ml/Kg to 40 ml/Kg for 20-60 minutes. No appreciable abnormalities were observed on the blood pressures and on the heart rates of the animals under the test.

In the analogous animal test as control in which the infusion preparation was used which contained the pullulan fraction having $\overline{M}w$ of about 90,000, a considerable abnormality was observed on the blood pressure of the animals under the test.

In another animal test in which two groups of the rabbits were employed consisting of five animals, each 40 ml/Kg of each of two preparations of the pullulan fractions at the concentrations of 6% (W/V) in a physiological saline were infused once a day for seven consecutive days into the individual animals of said respective groups. One of said preparations contained the refined pullulan having $\overline{M}w$ of 33,000 and the other contained the refined pullulan having $\overline{M}w$ of 40,000. As the results of the test, none of the animals showed reduction in food and water uptake or other toxic signs such as loss of body weight.

Desirable therapeutic effects represented by the preparations which contain the particular pullulan fractions specified in the present invention will be explained more in detail by the aid of the pharmacological experiments hereinaftermentioned along with the accompanying drawings, wherein:

FIG. 1-1 graphically shows the variations with the lapse of time of the polysaccharide contents in the serums of the rabbits to which 30 ml/Kg of the respective plasma expander preparations marked therein had been infused once a day for seven consecutive days.

Figures 1, 2:
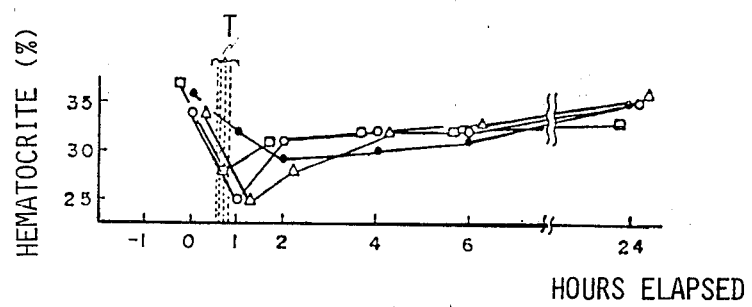

FIG. 1-2 graphically shows the variations with the lapse of time of the hematocrite values in the bloods of rabbits to which 30 ml/Kg of the marked respective plasma expander preparations the same as those indicated in FIG. 1-1 had been infused once a day for seven consecutive days.

FIG. 2 graphically shows the diminution rates (%) with the lapse of time of the indicated various plasma expanders in the bloods of rabbits to which 40 ml/Kg of said plasma expander preparations had been infused once a day for seven consecutive days.

FIG. 3 graphically shows the molecular weight distributions of three particular pullulans to be used for the animal test in order to inspect their molecular degradation and/or decomposition in the body. The pullulans used had the respective $\overline{M}w$'s given therein.

Figure 4:
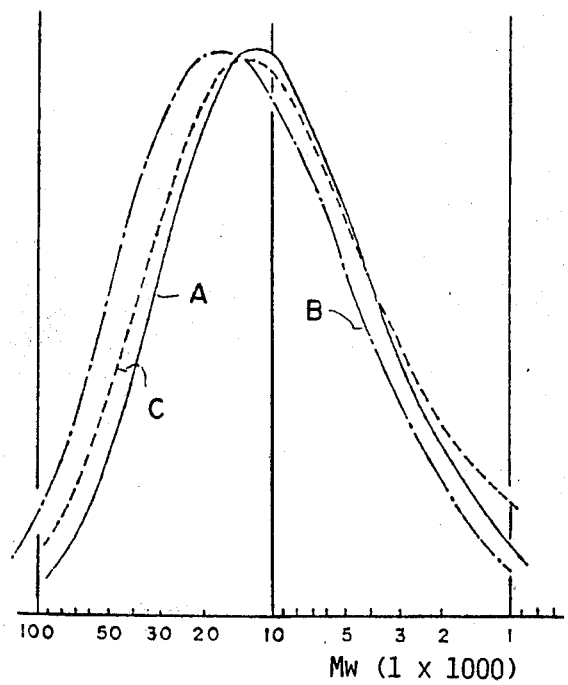

FIG. 4 graphically shows the molecular weight distributions of the polysaccharides contained in the urines excreted for 24 hours from the rabbits to which the three specified pullulan preparations had been infused respectively.

Figures 1, 5:
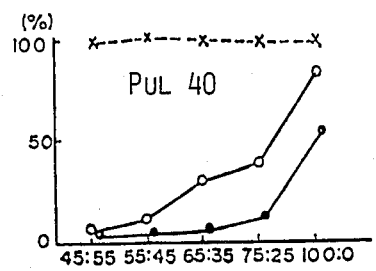
Figures 2, 5:
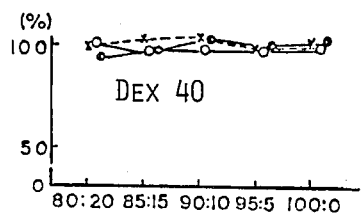

FIGS. 5-1 and 5-2 graphically show the amounts of the polysaccharides as the molecular degradation and decomposition products of the genuine Pul-40 and Dex-40, each having $\overline{M}w$ of 40,000, when these substances were cultivated by the aid of the kidney homogenate and the lung homogenate prepared from rats. Data of the blank tests as control are also included in the Figures.

Figure 7:
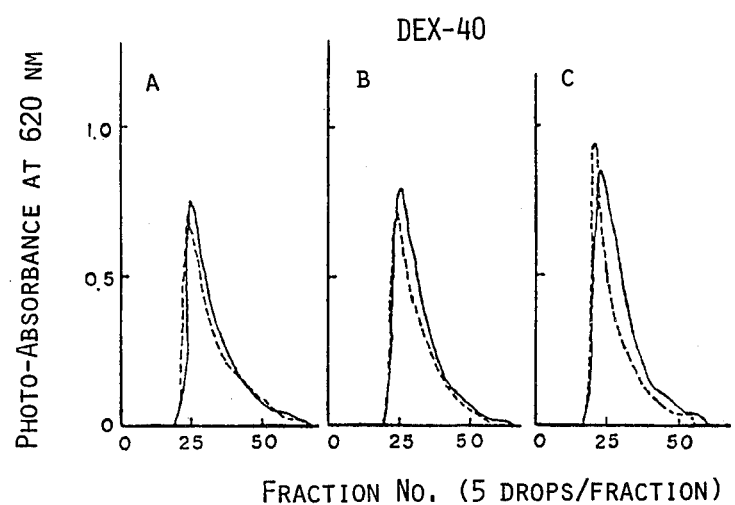

FIGS. 6 and 7 graphically show the fractional elution patterns through Sephadex G-50 columns having the dimension of 0.9 cm($\phi$)×10 cm(h) of the polysaccharides obtained in the abovementioned cultivations of said Pul-40 and Dex-40. Relation between the fraction number and the estimated molecular size is shown by "d". Data of the blank tests as control are also given in the Figures.

Figure 8:
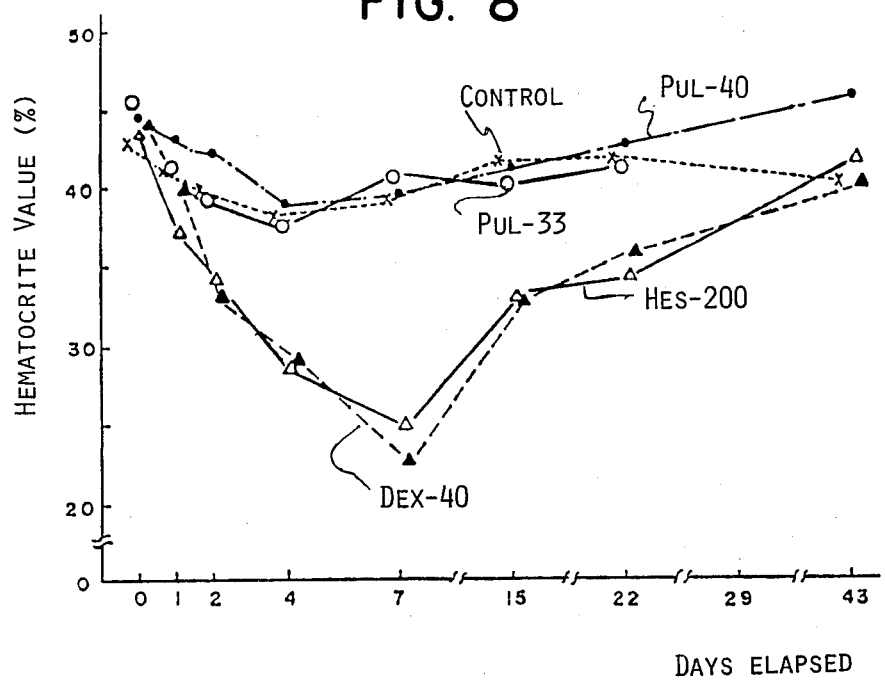

FIG. 8 graphically shows the variations with the lapse of time by the day of the hematocrit values in the bloods of rabbits to which 40 ml/Kg of each of the four given plasma expander preparations had been respectively infused once a day for seven consecutive days. Data of the blank test as control are also included in the Figure.

Figure 9:
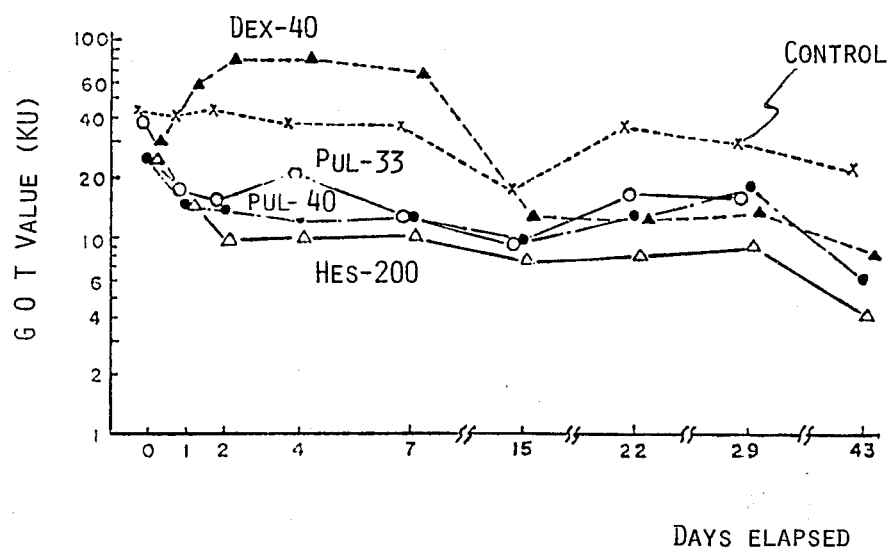

FIG. 9 graphically shows the variations with the lapse of the time by the day of the plasma glutamyl oxalo transaminase (G O T) values of the bloods of rabbits to which the four given plasma expander preparations had been infused at the rate of 40 ml/Kg once a day for seven consecutive days. The data of the blank test as control are also included in said Figure.

Details of the data given in FIGS. 1 to 9 are substantiated by the following pharmacological experiments:

(a) Effect of plasma expanders due to their retention in the blood

Two 5% (W/V) pullulan preparations in a physiological saline were prepared, one of which contained the refined pullulan having $\overline{M}w$ of 50,000, (Pul-50), and the other the refined pullulan having $\overline{M}w$ of 85,000, (Pul-85).

At the same time, a 6% (W/V) dextran preparation and a 10% (W/V) H E S preparation, both also in a physiological saline, were prepared for the sake of comparison, the former containing the dextran having $\overline{M}w$ of 40,000, (Dex-40), and the latter containing H E S having $\overline{M}w$ of 200,000, (H E S-200).

To four groups of rabbits, each group consisting of three male animals having an average body weight of 2.7 Kg, were infused separately the abovementioned four preparations. The infusions were carried out with 75 ml of the respective preparation for 20 minutes through the auricular veins of the respective animals.

After completion of the infusions, blood samples were periodically taken from the animals and the polysaccharide contents and the hematocrit values in the serums of said blood samples were estimated.

Estimation of the polysaccharide contents was conducted in accordance with the known precipitation method in which ethanol is employed as precipitant.

In FIG. 1—1, the resulting data relative to the variations of polysaccharide contents(%) with the lapse of time (by the hour) were plotted, wherein the respective values estimated immediately after the completion of the infusion for 20 minutes were established as the standard values of "100%". On inspection of the graphs, it is noted that the patterns of said variations due to the infusions of both the said 5% Pul-50 and Pul-85 preparations are fairly close to those brought about by the infusions of the said 6% Dex-40 and 10% H E S-200 preparations.

In FIG. 1-2, on the other hand, the resulting data relative to the variations of hematocrit values with the lapse of time (by the hour) were plotted on the graphs, the values having been measured after completion of the infusion for 20 minutes.

Lowering of hematocrit values, which occurs when polysaccharide is retained in the blood due to, for example, infusion of a plasma expander, is, as known, indicative of an increase in the quantity of plasma in the blood.

Now, from the data given in FIG. 1-2 with respect to the measured hematocrit values as mentioned above, it is appreciated that the plasma expanding effects represented by said two 5% pullulan preparations, like those represented by said Dex-40 and 10% H E S-200 preparations, last for six hours after completion of the infusions with an increase corresponding to approximately 7% expansion of the plasma on the basis of the plasma values corresponding to those measured before the infusions.

(b) Excretion ability of the plasma expanders from the body

It has been confirmed that excretion through renal glomerulus of the infused colloidal substance as the plasma expander, which takes place within a certain period of time after said infusion, mainly depends upon the magnitude of the molecular weight of said colloidal substance.

Based on this consideration, the following experiment was carried out in order to inspect the circumstances of excretion from the body of the infused plasma expanders including two pullulan preparations which contained respectively Pul-33 and Pul-40, and two other preparations as control, which contained respectively Dex-40 and H E S-200. The pullulans contained in the former preparations possess the narrower molecular weight distributions, especially compared to that of H E S-200.

Pul-33 having $\overline{M}w$ of 33,000 and Pul-40 having $\overline{M}w$ of 40,000 were separately dissolved in a physiological saline to produce the 6% Pul-33 and 6% Pul-40 preparations.

In the same manner as abovementioned, a 10% Dex-40 preparation and a 6% H E S-200 preparation both in a physiological saline were prepared. Dex-40 had $\overline{M}w$ of 40,000 and H E S-200 had $\overline{M}w$ of 200,000.

Twenty male rabbits were divided into four groups, each group consisting of five animals having an average body weight of 2.6 Kg.

The animals in every group were separately infused intravenously with one of the abovementioned four preparations in a dosage of 40 ml/Kg once a day for seven consecutive days. During and after the infusion period, blood samples were periodically taken from the animals, and the contents of the polysaccharides in the serums of the samples were estimated by means of the precipitation method with addition of ethanol. The results of the estimations were then calculated in terms of the diminution or consumption rates (%) based upon the initial quantities in the serums of polysaccharides corresponding to those of the essential ingredients contained respectively in the infused preparations. The values of the calculated diminutions were plotted in FIG. 2.

From FIG. 2, it is recognized that there occurred, at the time of 24 hours lapse from the completion of the total infusions, for example, about 95% diminution with respect to Pul-33 and about 85% diminution with respect to Pul-40. Similar diminution rates are observed throughout the course of the total infusions, and furthermore, 100% diminution took place after 8 days lapse from the final infusions, with respect to both these pullulans.

In contradistinction to the above considerations, it is recognized in FIG. 2 that about 65–67% diminution of the infused quantities of Dex-40 took place throughout the total infusions, and even after 15 days lapse since the final infusion, there occurred only about 80% diminution.

It is further recognized in the case of the infused H E S-200 that there occurred a poorer consumption, such as about 50–55% diminution, in the course of the infusions and only about 50% diminution even after 36 days lapse since the final infusion.

In addition to the above experiment, it was proved that the quantity of the polysaccharide recovered from the urine excreted in the course of the abovementioned infusions from the respective rabbits to which said H E S-200 preparation was infused, amounted only to about 50% of the quantity of the polysaccharide which was respectively recovered from the urines in the course of the abovementioned infusions from the animals to which the Pul-33 and Pul-40 preparations and the Dex-40 preparation were separately infused.

Superior excretion ability of the refined pullulan such as Pul-33 and Pul-40, as compared with those of the known plasma expanders such as Dex-40 and H E S-200 above referred to, is therefore acknowledged from the facts abovementioned.

(c) Molecular degradation and decomposition of pullulan (I) Experiment on molecular degradation and decomposition of pullulan infused into rabbits 100 ml each of three 5% (W/V) preparations, which respectively contained in a physiological saline the refined pullulan fractions having Mw's of 33,000, 50,000 and 85,000, were infused for 20 minutes into rabbits having an average body weight of 3 Kg. The urine excreted for 24 hours after the infusions were separately collected. Proteins were then removed from the urines, and the polysaccharides contained therein were precipitated with addition of five times the volume of acetone to the respective urine, and collected.

The molecular weight distributions of said three pullulan fractions contained in said three pullulan preparations are shown in FIG. 3, whereas the molecular weight distributions of the polysaccharides recovered from the urines were shown in FIG. 4.

As is noted in FIG. 4, the patterns of curves given therein are very similar to one another independent of the magnitudes of Mw of the parent pullulan fractions contained in the preparations, and further, most of said polysaccharides possess the molecular weights less than 60,000.

The abovementioned observations teach that the refined pullulan fractions such as those above referred to are gradually degraded in the body into polysaccharides having the relatively small molecular weights capable of easily passing through renal glomerulus into urines.

(II) Experiment on metabolism and decomposition of refined pullulan by the aid of tissues isolated from organs of the body Metabolism and decomposition of the refined pullulan caused by the tissues isolated from organs of the body were inspected by the use of the refined powdery pullulan having Mw of 40,000 (Pul-40) and the powdery Dex-40 as comparison. Both the powdery substances were separately mixed with a 50% (W/V) kidney homogenate, on the one hand, and with a 25% (W/V) lung homogenate, on the other. These homogenates had been prepared with rat organs. Four resulting mixtures were kept under incubation conditions at 37° C. for 24 hours. Toward the end of the incubation, the concentration of polysaccharide in the incubation mixtures amounted to 0.5% (W/V). Proteins separated out from the incubated mixtures were then removed, and the resulting four clear supernatant layers were respectively divided into five aliquots.

1 ml each of four ethanol:water mixtures consisting of the proportions (V/V) of 45:55, 55:45, 65:35 and 75:25 was added in regular order to four aliquots from among said five aliquots. These five aliquots were brought about from one of the abovementioned four clear supernatant layers. Here, the chosen supernatant layer was originated from the abovementioned incubation of Pul-40 by the aid of the kidney homogenate. To one remaining aliquot, nevertheless, were added 2 ml of absolute ethanol instead of one of the abovementioned ethanol:water mixtures.

All the precipitates thus formed respectively in the total five aliquots, the polysaccharides contained in said precipitates being different from one another, were separately recovered by centrifuge. In this centrifuge, the mother liquor from the aliquot to which 2 ml of the absolute ethanol had been added, was taken up and evaporated to dryness in order to recover any residue which may contain an additional polysaccharide. The residue obtained was then incorporated into the principal precipitate obtained by the centrifuge from said specific aliquot.

The amount of the polysaccharide in the respective precipitate was quantitatively estimated by means of the anthrone-sulfuric acid method.

The same exact operations were applied to the other five aliquots of the supernatant layer which originated from the Pul-40 incubation by the aid of the lung homogenate.

The results together with the results formerly obtained with respect to the other Pul-40 incubation by the aid of the kidney homogenate are graphically shown in FIG. 5-1.

Operations similar to those abovementioned were applied to the two sets of the five aliquots obtained from the other two supernatant layers, one of which was originated from the Dex-40 incubation by the aid of the kidney homogenate and the other was originated from the Dex-40 incubation by the aid of the lung homogenate, provided that four ethanol:water mixtures in the proportion (V/V) of 80:20, 85:15, 90:10 and 95:5 were used instead of the formerly used ethanol:water mixtures with respect to the incubations of Pul-40.

In this connection, the ethanol:water mixtures having the predominant ethanol contents, in contrast with the ethanol:water mixtures used in the case of the Pul-40 incubations, were used in the case of the Dex-40, because the mixtures of such a higher ethanol content were needed for complete precipitations from the supernatant layers originated from both the Dex-40 incubation mixtures.

Amounts of the polysaccharides finally obtained by the quantitative estimations in connection with said Dex-40 are graphically shown in FIG. 5-2.

From FIG. 5-1, it is noted that although the amount of polysaccharides estimated at the commencement of the incubations of Pul-40 are coincident with the amount of the polysaccharide obtained by the blank incubation test as control, which was conducted in a plain physiological saline with 0.9% concentration of Pul-40, the amounts of the polysaccharides finally obtained through the 24 hours incubation followed by the additions of the ethanol:water mixtures having the relatively low ethanol contents, are considerably small.

Again, from FIG. 5-1, it is further noted that the amount of polysaccharide, which was recovered from the precipitate obtained by the addition of 2 ml of absolute ethanol to the supernatant layer of the Pul-40 incubation liquor by the aid of the kidney homogenate, is computed to about 10% diminution, and about 40% diminution in the case of the Pul-40 incubation by the aid of the lung homogenate, both based upon the amount of the polysaccharide obtained through the blank test as control for Pul-40.

From these facts it is presumed that the specific pullulan defined in the present invention was metabolized by the aid of the tissue enzymes and was finally decomposed through glucose into gaseous carbon dioxide.

Contrary to the above, Dex-40, when incubated under the same conditions as those used in the incubations of Pul-40, was almost not metabolized or decomposed. There are no remarkable differences between the quantities of the polysaccharides recovered with the treatment of the specified ethanol:water mixtures, all having the ethanol contents above 80%, and also with absolute ethanol, (compare FIG. 5-2).

In view of the molecular weight distributions of the polysaccharides respectively recovered from the abovementioned incubation liquors of Pul-40 and Dex-40, which were established on the basis of the data of the fractional elution of said polysaccharides through a column of Sephadex G-50, it is considered that the molecular degradation predominantly took place only in the cases of incubations of Pul-40 (compare FIG. 6 in connection with Pul-40 and FIG. 7 in connection with Dex-40).

The above considerations support the foregoing presumption about the metabolism and decomposition of the pullulan defined in the present invention.

Similar phenomena of metabolism and decomposition were observed when the pullulan was incubated with the liver homogenate and serum taken from rats.

(d) Study on chronical administrations of the refined pullulan

Safety in successive chronical administrations of the refined pullulan in comparison with those shown by the hitherto known plasma expanders were carried out on male rabbits.

For carrying out the above study, there were used four preparations inclusive of two 6% pullulan preparations of Pul-33 and Pul-40, one 10% Dex-40 preparation and one 6% H E S-200 preparation. All of these preparations were the same as those used in the foregoing experiment on excretion ability of the plasma expanders.

Apart from the above, there was provided a plain physiological saline as control, which was the same as those used in the abovementioned preparations.

Intravenous infusions of the above preparations and the plain saline as control were effected in sequence for seven days with the dosage of 40 ml/Kg/day for 60 minutes to each of the rabbits divided into five groups, each group consisting of five animals having an average body weight of 2.6 Kg.

During and 24 hours after said infusions, the hematocrite values of the blood samples taken from the rabbits were measured. The data which resulted are plotted in FIG. 8.

As is evident from the graphs given in FIG. 8, the hematocrite values depressed slightly and continuously along with the progression of the infusions of both the pullulan preparations. The values equivalent to those measured at the commencement of the infusions, however, were restored in a relatively short time after completion of said infusions.

Different from the effects on the hematocrite values represented by the refined pullulans, said Dex-40 and H E S-200 preparations, when infused, led to considerable and rapid depression of the hematocrite values. Not only that, it required a good 35 days after the completion of the infusions, for the restorations of the hematocrite values equivalent to those of the original.

The variations in the different modes of the hematocrite values caused by the infusions of the abovementioned preparations thus teach that the named specific pullulans were excreted almost completely within say, 24 hours from the body subsequent to metabolism and decomposition after the infusions, while Dex-40 and H E S-200 accumulated as they were in the blood for about 24 hours after the infusions.

It is thus concluded that the refined pullulans as defined in the present invention are entirely safe for use in the treatment of hemorrhage.

The graphs given in FIG. 9, on the other hand, are concerned with the variations of the serum glutamyl oxalo trans-aminase values, that is, G O T values, of the animals, which were caused by the aforementioned infusions of said preparations. The G O T values in general are evaluated as one of the measures for the indication of cyto-toxity of liver cells.

As is seen in the graphs given in FIG. 9, there are no remarkable variations in the G O T values measured in the course of the chronical administrations of the Pul-33 and Pul-40 preparations and the H E S-200 preparation in comparison with the values obtained by comparative infusion as control of the plain physiological saline, which is the same as those used as the aqueous media in the three former preparations, although the former values are somewhat below the values of the control. On the contrary, a marked increase in the G O T values is observed in the case of the infusions of the Dex-40 preparation.

In this connection, it should be noted that the albumin:globulin ratio, in the case of the infusions of the Dex-40 preparation, was considerably lowered owing to an increase of the globulin value, on the one hand, and decrease of the albumin value, on the other. The observed symptom, which means an impediment of the liver function, is coincident with the standardized significations given in the pathological inspections on the organs in the body hereinundermentioned.

The animals employed in the abovementioned pathological inspections were slaughtered in order to carry out further pathological inspections on their organs. The results of the microscopic inspections are tabulated in the following Table, wherein the signs "−, ±, +, ++ and +++" were used to signify the extent of pathological changes observed such as necrosis in the hepatic cells, vacuolation in the renal tubles and fibrotic change in the cardiac muscles.

TABLE

| Preparation infused | Days elapsed, starting from infusion | liver | kidney | heart | lung | spleen |
|---|---|---|---|---|---|---|
| Saline (Control) | 7 | ± | − | − | − | − |
|  | 15 | − | − | − | − | − |
|  | 22 | ± | − | − | − | − |
|  | 29 | − | − | − | − | − |
|  | 43 | − | − | − | − | − |

TABLE-continued

| Preparation infused | Days elapsed, starting from infusion | liver | kidney | heart | lung | spleen |
|---|---|---|---|---|---|---|
| Pul-33 | 6 | − | − | − | − | − |
|  | 7 | ± | − | − | − | − |
|  | 15 | − | − | − | − | − |
|  | 22 | − | − | − | − | − |
|  | 29 | ± | − | − | − | − |
| Pul-40 | 7 | ± | − | − | − | − |
|  | 15 | − | − | − | − | − |
|  | 22 | − | − | − | − | − |
|  | 29 | − | + | − | − | − |
|  | 43 | − | − | − | − | − |
| Dex-40 | 7 | +++ | ++ | +++ | ++ | − |
|  | 15 | ± | + | − | − | − |
|  | 22 | ++ | − | − | − | − |
|  | 29 | +++ | − | − | − | − |
|  | 43 | + | − | − | − | − |
| HES-200 | 7 | − | − | − | − | − |
|  | 15 | ± | − | + | − | − |
|  | 22 | ++ | + | − | − | − |
|  | 29 | ++ | − | − | − | − |
|  | 43 | +++ | ++ | − | − | − |

Where, the signs denote:
− No change;
± Very slight change;
+ Slight change;
++ Fairly distinct change;
+++ Considerable change.

More precisely, no remarkable pathological changes, on the basis of the inspection results in the control, were observed in the organs of the animals to which the Pul-33 and Pul-40 preparations were infused, with the exception of a white deposit, like in the control, at the periphery of the liver.

On the contrary, several toxic signs were observed in the organs of animals infused with the Dex-40 preparation, such as increase in weight, atrophy of hepatic cells and scatter of myocarial fibrosis, all in the liver; vacuolation in the renal tubules; and blister-like tumor in the lung.

Some toxic signs were also observed in the organs of animals infused with the H E S-200 preparation, such as change in color to pale, dark white deposit at periphery, increase and cloudy swelling of heptic cells, all in the liver. Deposition of polysaccharide in the dilated renal tubles was also observed.

The following are some embodiments of the invention, which illustrate the isolation of the refined pullulan fractions and the preparation of the therapeutic preparations which contain said refined pullulan fractions.

(a) Isolation of the refined pullulan fractions:

EXAMPLE 1

A 10% (W/V) aqueous solution of a conventional pullulan, which is a product of Hayashibara Biochemical Laboratories, Inc., Okayama, Japan, was prepared by dissolving in water 200 g of said pullulan. The pH of the resulting solution was adjusted to about 2 with addition of hydrochloric acid. The solution was kept at the temperature of 80° C. for 2 hours to effect partial hydrolysis of the pullulan, followed by neutralization with addition of an aqueous solution of sodium hydroxide, and the whole was cooled.

The solution was then mixed with a sufficient amount of methanol to give a solution having a 40% (V/V) concentration of the latter and to cause separation of the solution into two layers. After removal of the lower layer, the upper layer was again mixed with fresh methanol until the final concentration of the latter was 55% (V/V), and the newly formed lower layer was collected. Throughout these procedures, the temperatures were kept at 30° C.

The methanol contained in the collected aqueous solution was removed by distillation. The resultant aqueous pullulan solution was decolorized with active carbon, deionized with ion-exchangers of H- and OH-forms, and finally filtered with a membrane filter. The filtrate containing the purified pullulan fraction having $\overline{M}w$ of 50,000, was concentrated by evaporation. The solid residue was dried and pulverized to yield about 90 g of the pyrogen-free white pullulan.

EXAMPLE 2

A 20% (W/V) aqueous pullulan solution prepared by dissolving 200 g of a commercial pullulan product in water was subjected to a partial hydrolysis in accordance with the same process as that used in the preceding Example. To the neutralized aqueous solution thus obtained, was added a sufficient amount of ethanol to give a 50% (V/V) concentration of the latter in order to separate the resulting solution into two layers. After removal of the lower layer, the upper layer was mixed with fresh ethanol until the final concentration of the latter was 70% (V/V), and the lower layer newly formed was collected. Throughout the procedures, temperatures were kept at 40° C.

Subsequent procedures were carried out similarly as those used in Example 1. A purified powdery pullulan having $\overline{M}w$ of 33,000 and free from pyrogen was obtained at the yield of about 70 g.

EXAMPLE 3

A 5% (W/V) aqueous pullulan solution prepared by dissolving 200 g of a commercial pullulan in water was subjected to a partial hydrolysis, and the resulting hydrolized aqueous solution was neutralized in accordance with the procedures given in Example 1.

To the solution was added a sufficient amount of acetone to give a 20% (V/V) concentration of the latter, whereupon the solution separated out into two layers. After removal of the lower layer, the remaining upper layer was mixed with fresh acetone to yield a 45% (V/V) concentration of the latter, and the lower layer newly formed was collected. Throughout the operations, the temperatures were kept at 30° C.

Subsequent procedures were carried out similarly as those used in Example 1. A purified powdery pullulan fraction having $\overline{M}w$ of 85,000 and free from pyrogen was obtained at the yield of about 80 g.

(b) Preparation of therapeutic pullulan preparations:

EXAMPLE 4

Sixty g of the refined pullulan having $\overline{M}w$ of 40,000 were dissolved in 1 liter of physiological saline. The resulting aqueous solution was filtered, and the filtrate was stirred with 0.05 g of active carbon. The mixture was again filtered to remove the spent active carbon. The aqueous solution of the pullulan was finally sterilized.

EXAMPLE 5

Fifty g of the purified pullulan having $\overline{M}w$ of 60,000 were dissolved in 1 liter of physiological saline, and the resulting aqueous solution was filtered. The filtrate was stirred with 0.05 g of active carbon, and filtered to remove the spent active carbon, and the filtrate was finally sterilized.

EXAMPLE 6

A mixture of 50 g of the refined pullulan having $\overline{M}w$ of 60,000, 50 g of glucose and 9 g. of sodium chloride was added to an amount of distilled water, and the whole was made up to 1 liter by further adding an adequate amount of distilled water.

The resulting aqueous pullulan solution was then treated in accordance with the processes in Example 4.

What is claimed is:

1. A sterile, isotonic solution containing 4 to 10% w/v of a refined pullulan having a molecular weight distribution within the range of from 30,000 to 90,000.

2. A solution as claimed in claim 1, prepared by a process which comprises:
   (1) dissolving in water a pullulan having a molecular weight distribution outside the range of from 30,000 to 90,000,
   (2) adding to the resulting aqueous solution a water-miscible organic solvent in an amount sufficient to produce an aqueous mixture which contains 20 to 50% v/v of the organic solvent, and separating the mixture into an upper layer and a lower layer,
   (3) recovering the upper layer,
   (4) adding to the recovered upper layer another portion of said organic solvent in an amount sufficient to produce an aqueous mixture which contains 40 to 70% v/v of the organic solvent, and separating the mixture into an upper layer and a lower layer,
   (5) recovering the lower layer from step (4),
   (6) isolating a refined pullulan from the recovered lower layer, said refined pullulan having a molecular weight distribution within the range of from 30,000 to 90,000,
   (7) dissolving said refined pullulan in physiological saline to produce an isotonic solution which contains from 4 to 10% w/v of the refined pullulan, and
   (8) sterilizing the isotonic solution.

3. A process for preparing a solution as claimed in claim 1 which comprises:
   (1) dissolving in water a pullulan having a molecular weight distribution outside the range of from 30,000 to 90,000,
   (2) adding to the resulting aqueous solution a water-miscible organic solvent in an amount sufficient to produce an aqueous mixture which contains 20 to 50% v/v of the organic solvent, and separating the mixture into an upper layer and a lower layer,
   (3) recovering the upper layer,
   (4) adding to the recovered upper layer another portion of said organic solvent in an amount sufficient to produce an aqueous mixture which contains 40 to 70% v/v of the organic solvent, and separating the mixture into an upper layer and a lower layer,
   (5) recovering the lower layer from step (4),
   (6) isolating a refined pullulan from the recovered lower layer, said refined pullulan having a molecular weight distribution within the range of from 30,000 to 90,000,
   (7) dissolving said refined pullulan in physiological saline to produce an isotonic solution which contains from 4 to 10% w/v of the refined pullulan, and
   (8) sterilizing the isotonic solution.

* * * * *